United States Patent
Bani-Hashemi et al.

(10) Patent No.: US 6,473,489 B2
(45) Date of Patent: *Oct. 29, 2002

(54) APPARATUS FOR SUPERIMPOSITION OF X-RAY AND VIDEO IMAGES

(75) Inventors: Ali Bani-Hashemi, Belle Mead; Nassir Navab, E. Windsor, both of NJ (US); Matthias Mitschke, Nuremberg (DE)

(73) Assignee: Siemens Corporate Research, INC, Princeton, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/410,225

(22) Filed: Sep. 30, 1999

(65) Prior Publication Data
US 2002/0012420 A1 Jan. 31, 2002

(51) Int. Cl.[7] .............................. A61B 6/08; G01N 23/04
(52) U.S. Cl. ........................ 378/63; 378/206; 378/98.12
(58) Field of Search ........................... 378/63, 206, 205, 378/98.12

(56) References Cited

U.S. PATENT DOCUMENTS

| | | | | |
|---|---|---|---|---|
| 4,246,607 A | * | 1/1981 | Vijverberg | 378/63 |
| 5,590,170 A | * | 12/1996 | Zweig | 378/63 |
| 6,227,704 B1 | * | 5/2001 | Bani-Hashemi et al. | 378/206 |
| 6,229,873 B1 | * | 5/2001 | Bani-Hashemi et al. | 378/206 |

FOREIGN PATENT DOCUMENTS

| | | | | |
|---|---|---|---|---|
| EP | 157688 | * | 10/1985 | 378/63 |
| JP | 54-158984 | * | 12/1979 | 378/63 |

* cited by examiner

Primary Examiner—Drew A. Dunn
(74) Attorney, Agent, or Firm—Adel A. Ahmed

(57) ABSTRACT

Superimposed X-ray and video images can be obtained by acquiring the respective images from the optically equivalent points in space. One or more mirrors may be used to acquire the images and direct them towards the camera. The images can then be combined by warping one onto the other.

7 Claims, 4 Drawing Sheets

APPARATUS FOR SUPERIMPOSITION OF X-RAY AND VIDEO IMAGES

CROSS-REFERENCE TO RELATED APPLICATION

This application is related to the following applications simultaneously filed by the same inventors and incorporated by reference herein:

a) Method for Aligning and Superimposing X-ray and Video Images;

b) Method for Aligning an Apparatus for Superimposing X-ray and Video Images; and c) Laser-Based Method for Aligning Apparatus for Superimposing X-ray and Video Images.

BACKGROUND OF THE INVENTION

In addition to X-ray images of an object, it is often useful to have a corresponding video image. If the two could be combined into a composite image, then one could immediately see how the features revealed by the X-ray relate to the surface features displayed in a video image.

DESCRIPTION OF THE INVENTION

One method of correlating a video image with an X-ray image of the same object is by acquiring the respective images from the same point in space. A video or optical camera can be placed at a point in space equivalent to that of the X-ray source by deflecting a portion of the optical image with an X-ray transparent mirror. The camera is oriented by an alignment procedure to insure that it is located at a point optically equivalent to the location of the X-ray source.

Figure 1:
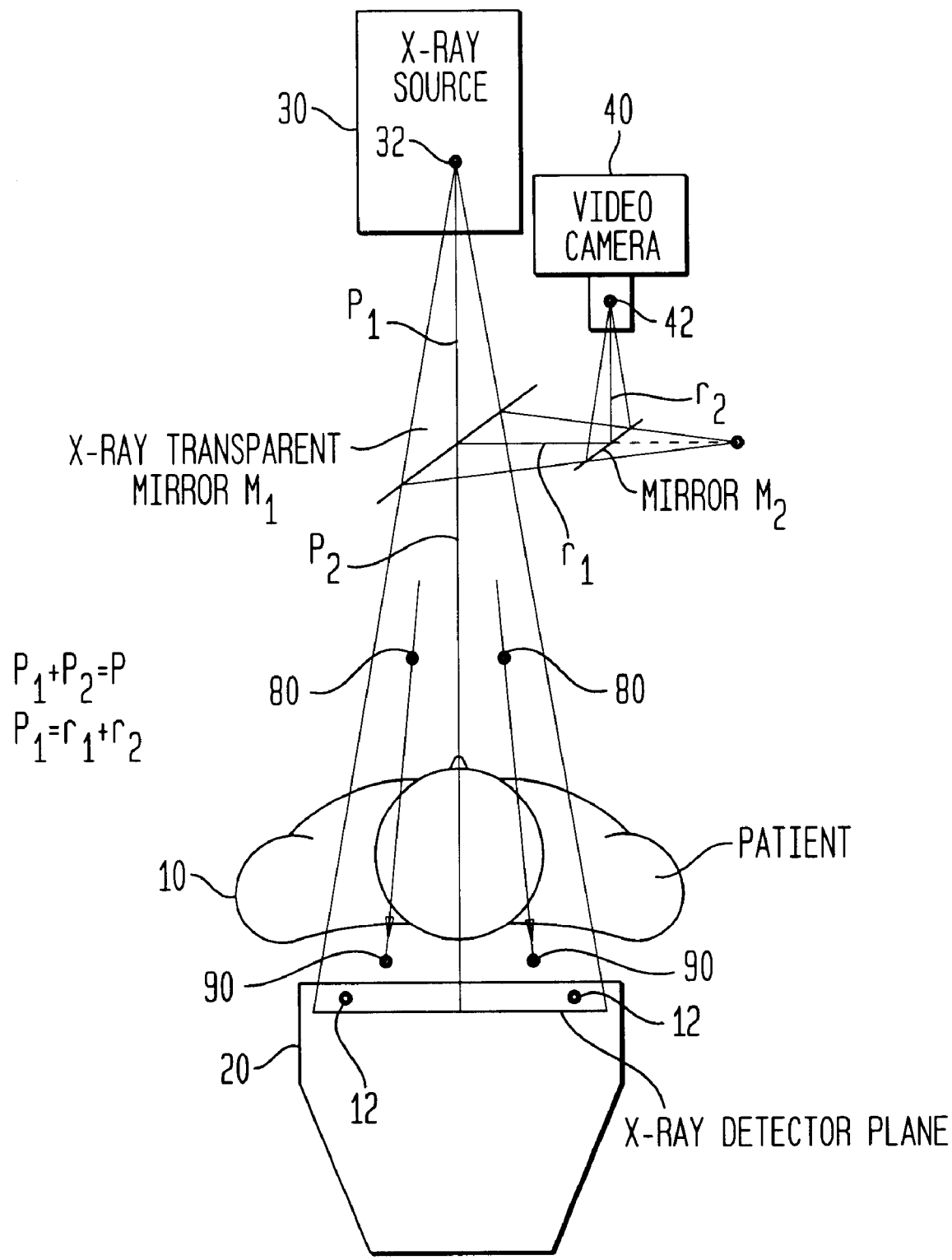
FIG. 1 is a conceptual diagram of the system.

In FIG. 1, a patient 10 is lying on a platform under which there is an X-ray detector plane 20. An X-ray source 30 located above the patient emits X-ray energy from a point in space defined as a projection center 32. The energy passes through the patient to the X-ray detector plane 20 to create an X-ray image. An optical camera 40, such as a video camera, is also positioned to obtain an image that may be combined with the X-ray image to create a composite visual and X-ray image.

To obtain a video image that can be combined with the X-ray image, the optical center 42 of the video camera 40 is positioned at effectively the same point in space as the projection center 32 of the X-ray source 30. Additionally, the optical axis of the camera 40 will also be aligned with an imaginary line running between the X-ray source projection center 32 and the center of the X-ray detector plane 20. Since the X-ray source 30 and the video camera 40 cannot physically occupy the same space, mirrors are employed to provide the video camera 40 a vantage point or point of projection effectively the same as that of the X-ray source 20.

A mirror M1, transparent to X-rays but reflective at visual wavelengths, is placed in the path of the X-ray source 30 at some angle, to deflect an optical image to a point away from the X-ray path. A second mirror M2 can be positioned in the path of the reflected image, again at an angle, to deflect the optical image towards the video camera 40. In FIG. 1, both mirrors M1 and M2 are at 45E with respect to the path of the X-ray source 30, although other angles could be employed. Thus, the visual image reflects off the surface of the mirror m1 and is again reflected by mirror M2.

The location of the mirrors can be selected such that the length of the segment r1 between mirrors M1 and M2 plus the length of the segment between the mirror M2 and the optical center 42 of the video camera 40 is equal to the distance from the mirror M1 to the center of X-ray projection 32 of the X-ray source 30.

Alternatively, the second mirror M2 could be dispensed with if the video camera 40 was positioned to one side of the X-ray path. Also, instead of using mirrors, a prism structure or another X-ray transparent light-bending mechanism could be employed to obtain the desired optical path length and angle of deflection.

Even with careful alignment of the mirrors M1 and M2, it may be difficult to co-locate the X-ray source projection center 32 and the camera's optical center 42 at the equivalent point in space with any degree of precision. Thus, some means of accurately positioning the camera 40 with respect to the X-ray source 30 is desirable.

Two methods for correlating the two images use the procedure of warping one two-dimensional image on a first plane onto a second plane. The X-ray detector plane 20 is provided with a reference device such as a pattern of markers 12 arranged in a square or some other suitable configuration. In lieu of a marker, the borders of the X-ray image may be utilized. The markers 12, fabricated from a material such as steel, appear as a series of dark point images in the X-ray and video images. Based on the aspect of the pattern of the markers 12 in the image that will be warped, the transformation that must be performed to warp the image to the second plane can be readily determined.

Warping of the X-ray image from the X-ray detector plane 20 to the video image of the markers 12 is accomplished by applying a planar transformation H to the X-ray image of the markers 12 such that it conforms to the aspect and dimensions of the pattern of the markers 12 as it appears in the video image. For each pixel in the X-ray image on the X-ray detector plane 20, matrix H calculated for the particular location of the X-ray detector plane 20 is multiplied by the position of that pixel to produce the position of the corresponding pixel in the video image.

The warping operation can be represented by the following equation:

$$m_i N = H m_i$$

where:

$m_i N$ are the pixels in the video image;

H is the planar transformation matrix mapping pixels in the X-ray image to the video image; and $m_i$ are the pixels in the X-ray image.

The matrix H is calculated by using techniques well known in the art. Such methods are described in U.S. Pat. Nos. 5,821,943 and 5,845,639, incorporated herein by reference, and in Wolberg, "Digital Image Warping," IEEE Computer Society Press, Los Alamitos, Calif. 1990.

In the both of the methods utilizing warping, at least two additional markers 80 are positioned off the detector plane 20 between the X-ray source 30 and the X-ray detector plane 20 (see FIG. 1). One way of accomplishing this is to place the "off-plane" markers 80 on a piece of plexiglass above the X-ray detector plane 20.

Figure 2:
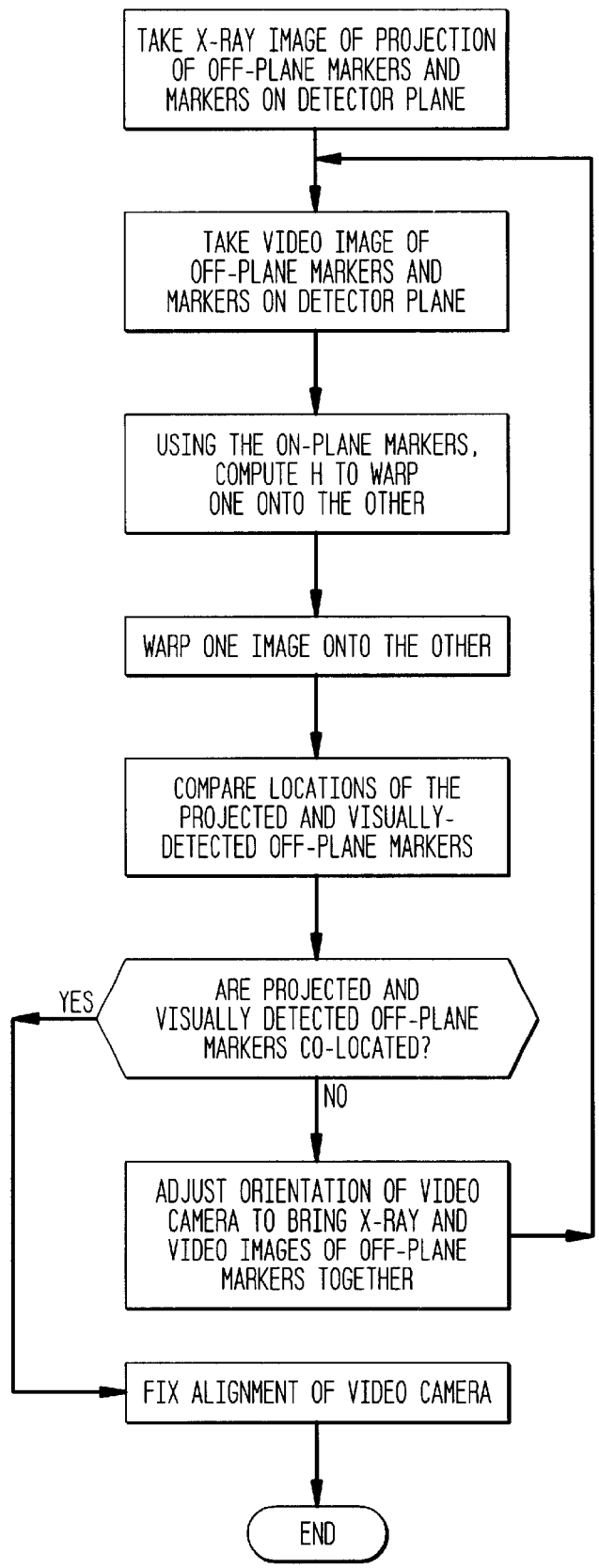
FIGS. 2 and 3 are flow charts of procedures for aligning the video camera.

In the first of these methods, illustrated in the flow chart of FIG. 2, an X-ray image is taken of the off-plane markers 80 as well as the markers 12 on the X-ray detector plane 20. Next, a video image is taken of the off-plane markers 80 and the markers 12 on the X-ray detector plane 20. Using the video image of the markers 12 on the X-ray detector plane 20, a value for H is computed. Then, the X-ray image is warped onto the video image, and the locations of the projected and visually-detected off-plane markers 80 are compared. If these locations coincide, the optical center 42 of the video camera 40 is then at a point in space equivalent to that of the projection center 32 of the X-ray source 30. However, if these locations do not coincide, then the orientation of the video camera 40 is adjusted to bring its optical center 42 towards the projection center 32 of the X-ray source 30. The process is repeated until the images coincide and the orientation of the video camera 40 is then fixed.

Figure 3:
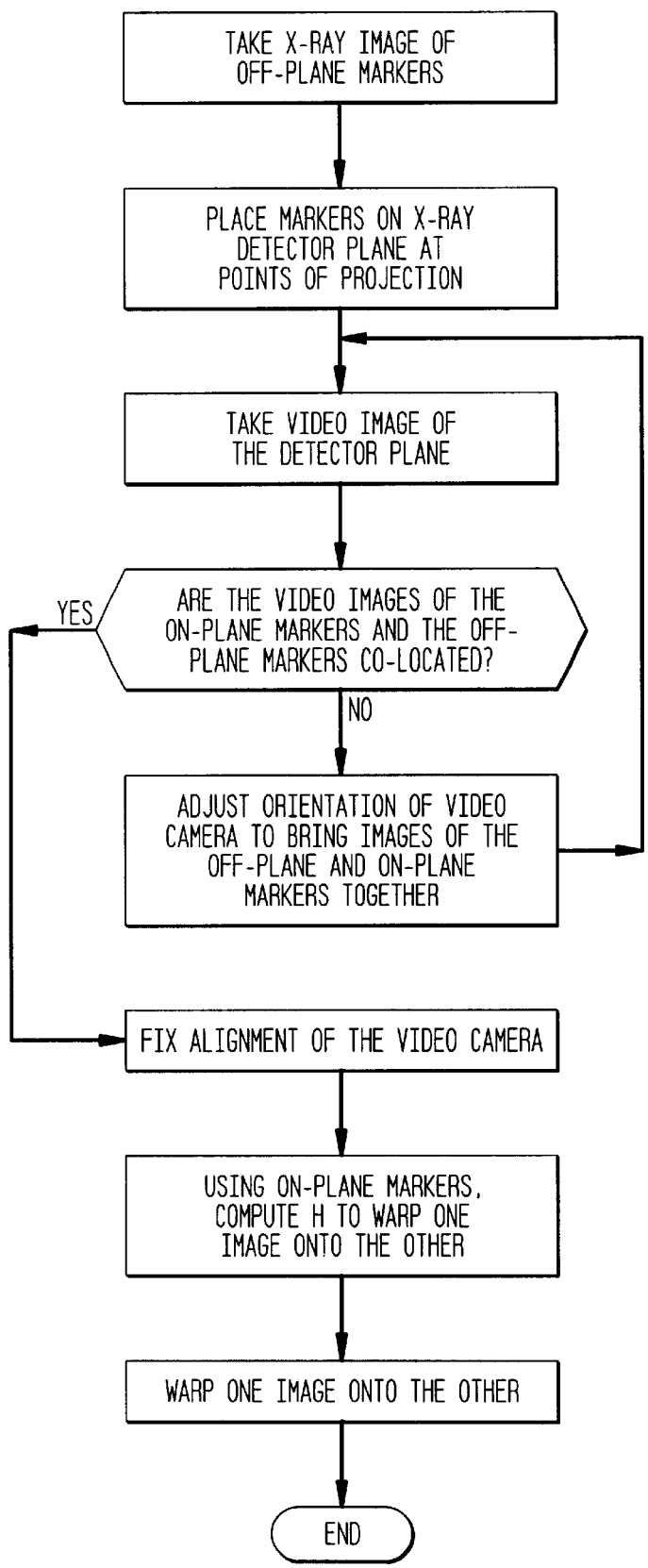

In the second of these methods, shown in the flow chart of FIG. 3, an X-ray image is taken of the off-plane markers 80. Then, a second set of markers 90, which will be referred to as "projection markers," are placed on the X-ray detector plane 20 at the points at which the off-plane markers 80 are projected by the energy from the X-ray source 30. On an X-ray image, therefore, the off-plane markers 80 and the corresponding on-plane projection markers 90 will appear as one on the X-ray image.

Now, a video image is taken of the X-ray detector plane 20. Since the off-plane markers 80 are suspended above the detector plane 20, they will also appear in the video image. The video image is examined to determine whether the video images of the on-plane projection markers 90 coincide with the corresponding off-plane markers 80. If they do, then the optical center 42 and projection center 32 effectively share the same point in space. If, however, the images do not coincide, then the orientation of video camera 40 is adjusted to bring the images of the off-plane markers 80 and on-plane projection markers 90 together, and another video image is acquired and evaluated, repeating until the images coincide, at which point the orientation of the camera is fixed. Finally, using the on-plane markers 12, a value of H is computed and the X-ray image is warped onto the video image to achieve superimposition.

Figure 4:
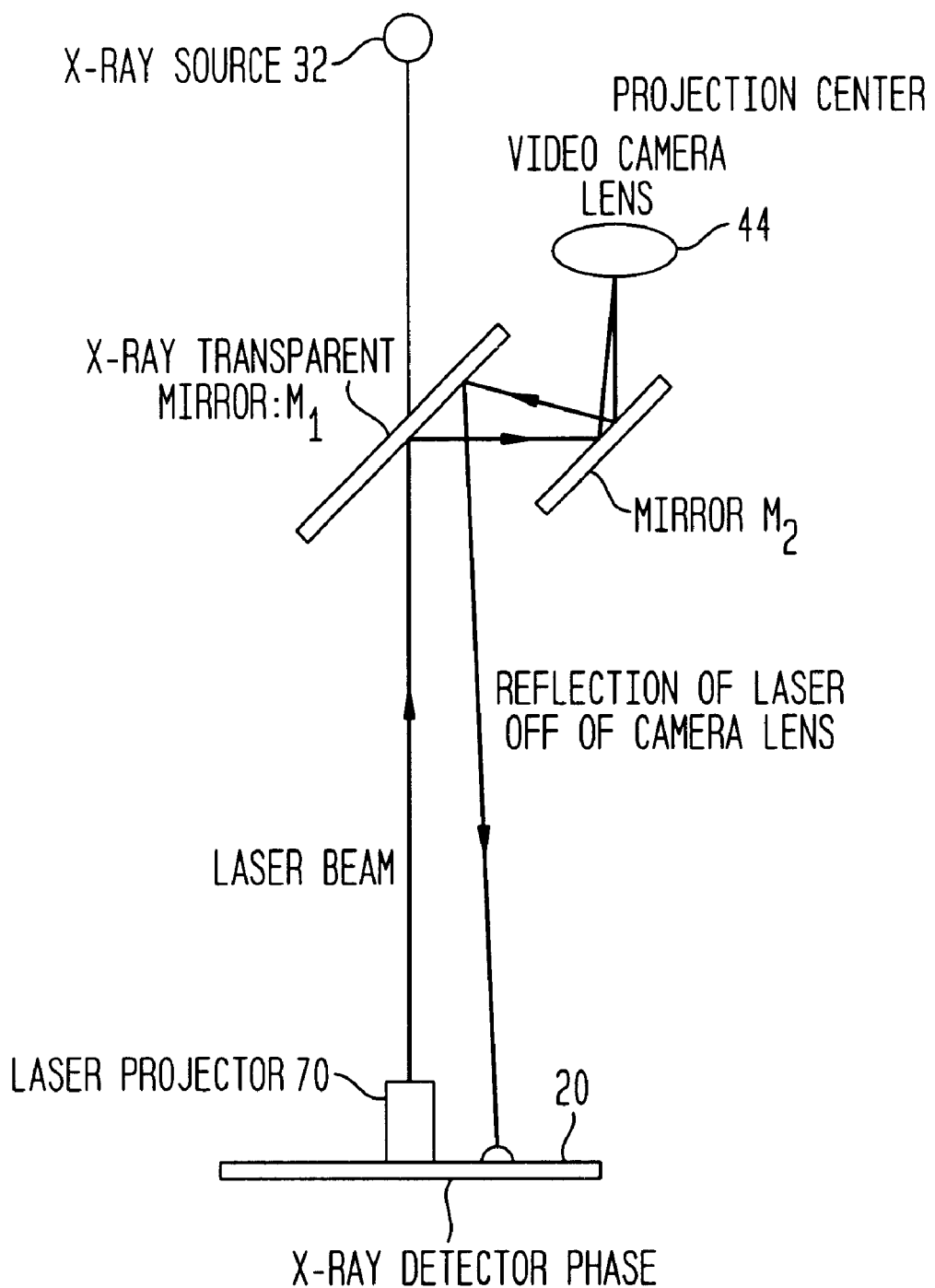
FIG. 4 is a diagram of a laser alignment system.

A third method for positioning the video camera 40 uses a laser. A source 70 of laser light is placed at the center of the X-ray detector plane 20 and aimed at the projection center 32 of the X-ray source 30, as shown in FIG. 4.

The mirrors M1 and M2 reflect the laser light causing it to travel to the video camera 40 and reflect off the surface of lens 44 of the video camera 40. The position of the video camera 40 is adjusted until the laser light returning to the source 70 is coincident (or nearly coincident) with the light issuing from the source 70. This may be confirmed visually by observing where the reflected beam lands on the X-ray detector plane 20. To align the images and achieve superimposition, the X-ray image can then be warped onto the video image.

Variations of the foregoing may be employed to suit the application. For example, one may use two X-ray source and video camera combinations to achieve a stereo representation of the object of interest. In lieu of the off-plane markers 80, on may substitute any object or objects that presents at least two points of reference visible by X-ray and optically. Also, instead of warping the X-ray image onto the video image, one could warp the video image onto the X-ray image, to achieve superimposition. In the configurations discussed above, the optical image is acquired by a video camera. In reality, any optical camera—still, digital, CCD, or other—may be employed with the apparatus and method described above. Additionally, X-ray images should be understood to include single, X-ray exposures as well as real-time, X-ray fluroscopic exposures. Finally, it should be understood that the methods described here may be executed in real time.

What is claimed is:

1. A method of correlating an optical image with an X-ray image by superimposing one image on the other, said method comprising the steps of:

directing a source of X-ray energy from a point in space through an object of interest onto a detector plane, creating an X-ray image on the detector plane;

positioning the optical center of an optical camera at a point in space equivalent to the projection center of the X-ray source;

obtaining an optical image of the object of interest from an optically equivalent point in space;

superimposing the X-ray and optical images; and warping one of the images onto the other, such that said images coincide in magnification and such that said images have a common image plane with each other.

2. The method of claim 1 where the step of superimposing occurs in real-time.

3. The method of claim 1 wherein the step of positioning the optical center of the optical camera comprises a step of positioning at least one mirror, transparent to X-ray energy between the X-ray source and the object.

4. An apparatus comprising:

means for directing a source of X-ray energy from a point in space through an object of interest onto a detector plane, creating an X-ray image on the detector plane;

optical means for obtaining an optical image of the object of interest from an optically equivalent point in space;

means for positioning the optical center of said optical means at a point in space equivalent to the projection center of the X-ray source;

means for superimposing the X-ray and optical images; and means for warping one of the images onto the other, such that said images coincide in magnification and such that said images have a common image plane with each other.

5. An apparatus as set forth in claim 4, where the means for superimposing accomplishes said superimposing in real time.

6. An apparatus as set forth in claim 4, where the optical means comprises an optical camera.

7. An apparatus as set forth in claim 1, where the means for positioning the optical means at a point in space equivalent to the projection center of the X-ray source comprises at least one mirror, transparent to X-ray energy, positioned between the X-ray source and the object.

* * * * *